US00PP31982P2

(12) United States Plant Patent
Van Dijk

(10) Patent No.: US PP31,982 P2
(45) Date of Patent: Jul. 14, 2020

(54) ***ANTHURIUM* PLANT NAMED 'ANTHATEIP'**

(50) Latin Name: ***Anthurium andraeanum* L.**
Varietal Denomination: ANTHATEIP

(71) Applicant: ANTHURA B.V., Bleiswijk (NL)

(72) Inventor: Jan Van Dijk, Bleiswijk (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 16/501,632

(22) Filed: May 14, 2019

(51) Int. Cl.
*A01H 5/02* (2018.01)
*A01H 6/10* (2018.01)

(52) U.S. Cl.
USPC ..... Plt./365

(58) Field of Classification Search
USPC ..... Plt./365, 369
CPC ... A01H 5/02; A01H 5/00; A01H 5/12; A01H 6/00; A01H 6/10
See application file for complete search history.

(56) References Cited

PUBLICATIONS

Anthura Anthurium pot plant catalogue 2019/2020, retrieved on Jan. 22, 2020, retrieved from the Internet at https://www.deplantis.it/website/wp-content/uploads/2019/10/PAA_productcatalogue_2019.pdf, pp. 1-2,43,61. (Year: 2020).*
Flora-Ned B.V. Kwekersaanbod-week-50.pdf, 2013, retrieved on Jan. 22, 2020, retrieved from the Internet at http://www.floraned.nl/wp-content/uploads/2013/12/Kwekersaanbod-week-50.pdf, 3 pp. (Year: 2013).*
Upov Pluto Plant Variety Database Jan. 22, 2020, retrieved on Jan. 22, 2020, retrieved from the Internet at https://www.upov.int/pluto/en/index.jsp, one page. (Year: 2020).*
EU Community Plant Variety Rights Application No. 2016/2945, Application n°A201603030, filed Nov. 25, 2016, 8 pages.
EU Community Plant Variety Office Official Gazette, 1.2017, Feb. 15, 2017, cover page and pp. 30, 51.
EU Community Plant Variety Rights Certificate on the Grant No. EU 49802, issued Jul. 2, 2018, 2 pages.
EU Community Plant Variety Rights Application No. 2011/2792, Application n°A201101298, filed Nov. 21, 2011, 7 pages.
EU Community Plant Variety Office Official Gazette, 1.2012, Feb. 15, 2012, cover page and pp. 27, 47.
EU Community Plant Variety Rights Certificate on the Grant No. EU 34819, issued Apr. 8, 2013, 3 pages.

* cited by examiner

*Primary Examiner* — June Hwu
(74) *Attorney, Agent, or Firm* — Jondle & Associates, P.C.

(57) ABSTRACT

A new *Anthurium* plant named 'ANTHATEIP' particularly distinguished by having shiny, blistered, bright red, orbicular-cordate, and very durable spathes that retain the original color for a very long period of time, dark green and ovate-cordate, durable leaves, white spadices with yellow tips, early and rich flowering continuously throughout the year, and a plant height of 40.0 cm to 45.0 cm is disclosed.

3 Drawing Sheets

Genus and species: *Anthurium andraeanum* L.
Variety denomination: 'ANTHATEIP'.

BACKGROUND OF THE NEW PLANT

The present invention comprises a new and distinct variety of *Anthurium*, botanically known as *Anthurium andraeanum* L., and hereinafter referred to by the variety name 'ANTHATEIP'. The new *Anthurium* plant is a product of a planned breeding program conducted by the inventor in Bleiswijk, the Netherlands. The objective of this breeding program was to create a new plant with a height of 40.0 cm to 45.0 cm having shiny and blistered, bright red, orbicular-cordate, and very durable spathes.

The new variety originated from a cross-pollination made in December 2010 in Bleiswijk, the Netherlands. The female parent was a red *Anthurium* pot plant designated '16232-01' (unpatented), and the male parent was a red *Anthurium* pot plant designated '10953-02' (unpatented).

A single plant was selected from the progeny of the stated cross in November 2012. Asexual reproduction of the new variety by tissue culture obtained from callus culture originated on pieces of young leaves in 2015 in Bleiswijk, the Netherlands, has demonstrated that the new variety reproduces true to type with all of the characteristics, as herein described, firmly fixed and retained through successive generations.

Plant Breeder's Rights for this variety have been applied for in the European Union on Nov. 25, 2016, by Applicant who obtained the subject matter disclosed directly from the Inventor. 'ANTHATEIP' has not been made publicly available or sold anywhere in the world more than one year prior to the effective filing date of this application.

SUMMARY OF THE INVENTION

The following are the most outstanding and distinguishing characteristics of this new variety when grown under normal horticultural practices in Bleiswijk, the Netherlands:

1) Shiny and blistered, bright red, orbicular-cordate spathes;
2) White spadices with yellow tips; and
3) Green, ovate-cordate leaves.

DESCRIPTION OF THE PHOTOGRAPHS

This new *Anthurium* plant is illustrated by the accompanying photographs which show the overall plant habit including blooms and foliage of the plant; the colors shown are as true as can be reasonably obtained by conventional photographic procedures. The photographs are of a 44-week-old plant grown in a greenhouse in Bleiswijk, the Netherlands, in February 2019. Colors in the photographs may differ from the color values cited in the detailed botanical description, which accurately describe the actual colors of the new variety.

DESCRIPTION OF THE NEW VARIETY

Figure 1:
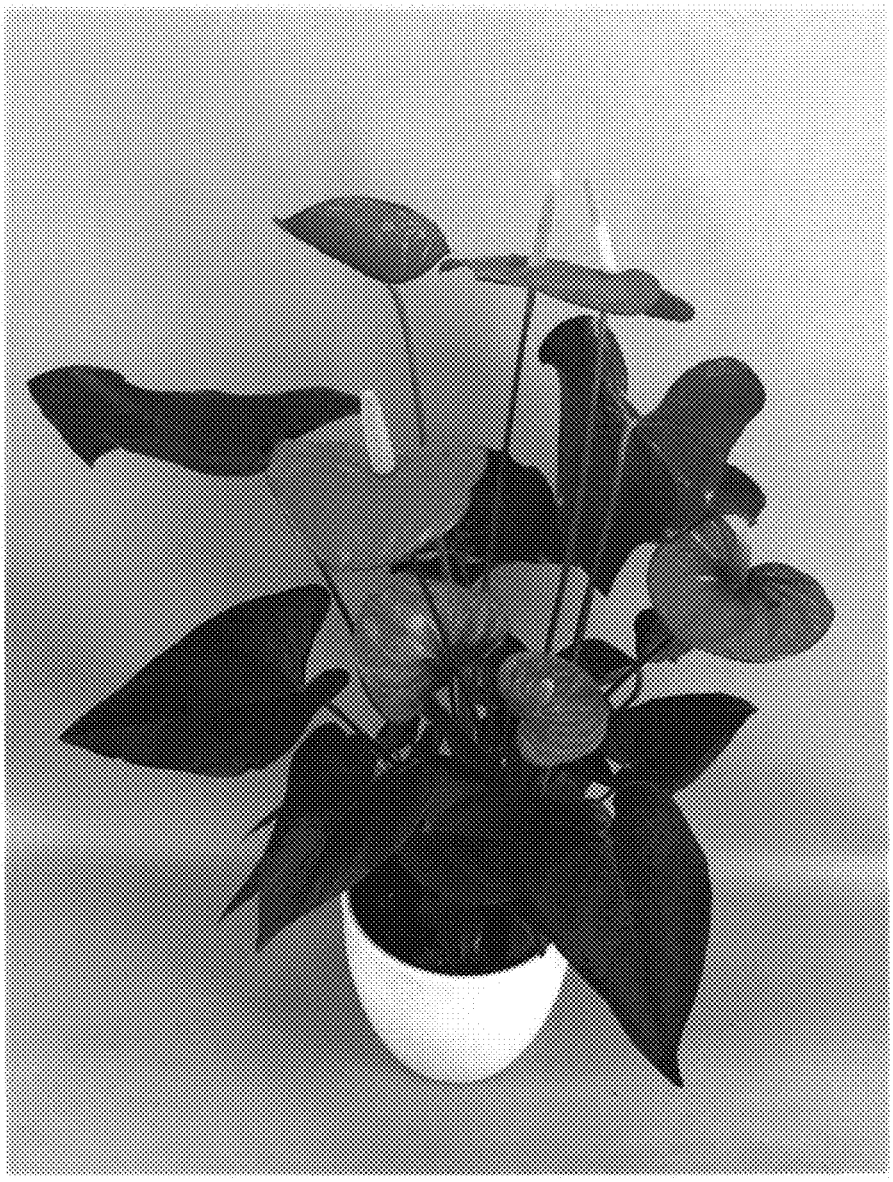
FIG. 1 shows the overall plant habit, including blooms and foliage.
Figure 2:
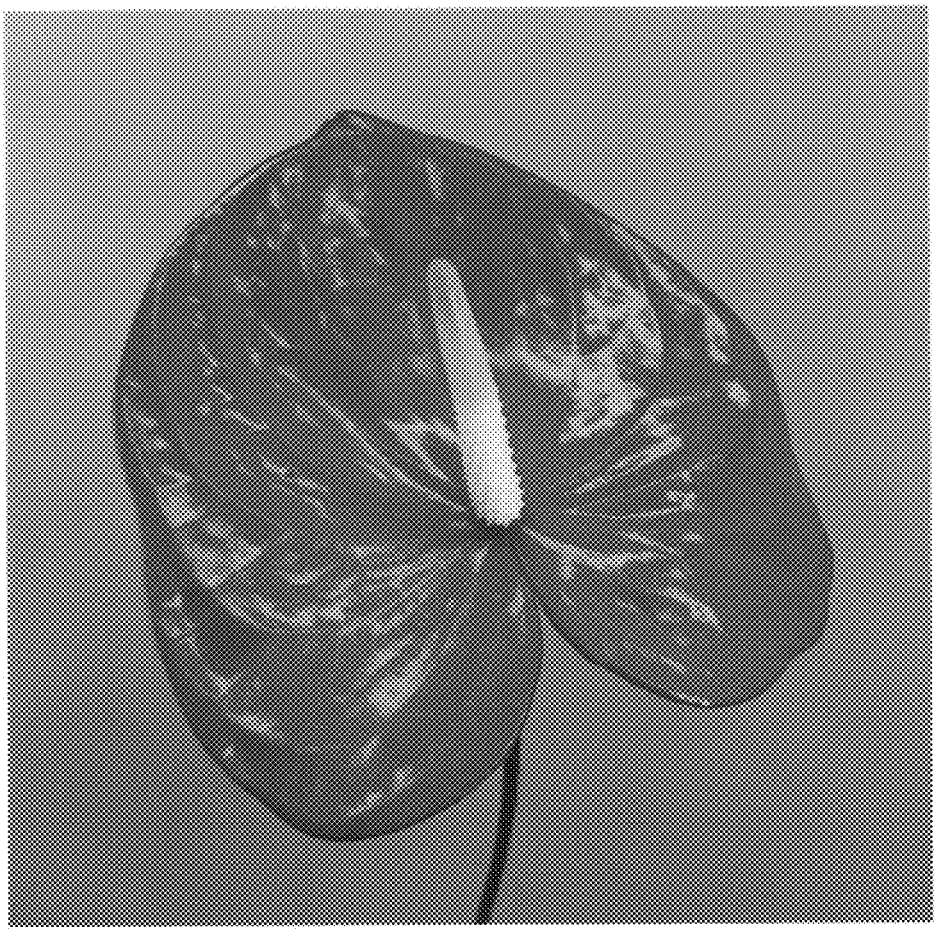
FIG. 2 shows a close-up of the mature spathe.
Figure 3:
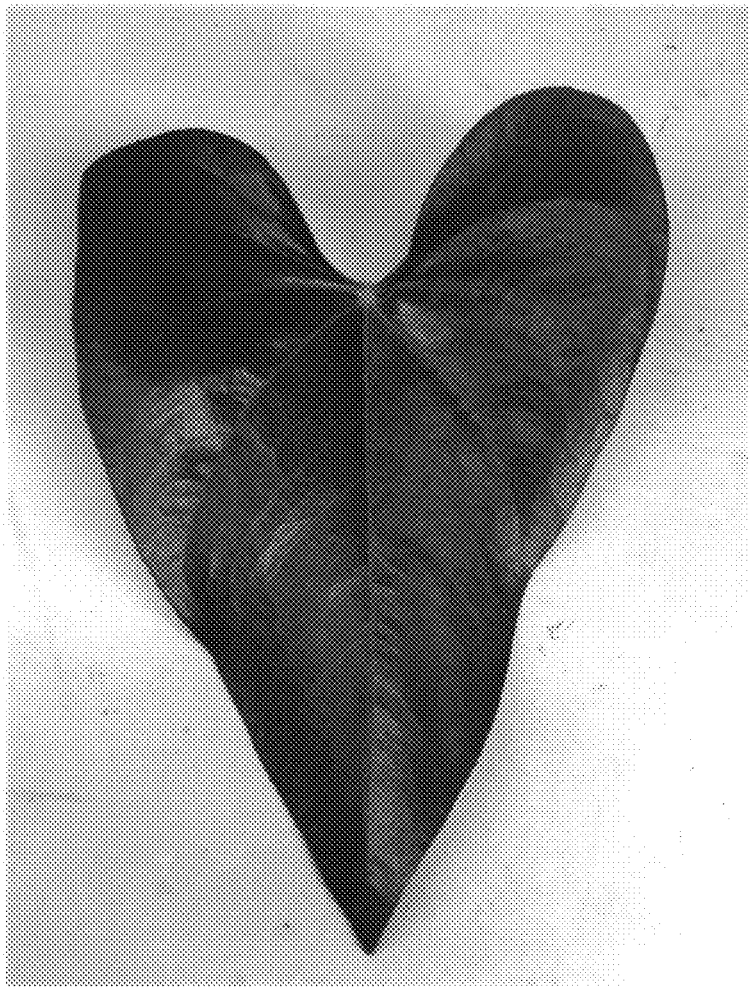
FIG. 3 shows a close-up of the upper leaf blade surface.

The following detailed description sets forth the distinctive characteristics of 'ANTHATEIP'. The data which define these characteristics were collected from asexual reproductions carried out in Bleiswijk, the Netherlands. The plant history was taken on 44-week-old plants which were planted from tissue culture in 14-centimeter (diameter) pots and grown in a glass greenhouse between 19° C. and 24° C. Observations were made in February 2019. Color readings were taken under 5000 lux natural light in the greenhouse. Color references are primarily to The R.H.S. Colour Chart of The Royal Horticultural Society of London (R.H.S.) (2015).

DETAILED BOTANICAL DESCRIPTION

Classification:

*Family*.—Araceae.

*Botanical*.—*Anthurium andraeanum* L.

*Common name*.—*Anthurium*.

*Denomination*.—'ANTHATEIP'.

Parentage:

*Female parent*.—*Anthurium* plant '16232-01' (unpatented).

*Male parent*.—*Anthurium* plant '10953-02' (unpatented).

Plant:

*Propagation*.—Tissue culture.

*Root description*.—Fleshy, yellowish-pink colored roots with small hairy lateral roots having yellow colored root tips.

*Time to produce a finished flowering plant*.—42 to 46 weeks after planting in a 14-cm (diameter) pot.

*Growth habit*.—Upright.

*Height* (*measured from soil, including inflorescence*).—40.0 cm to 45.0 cm.

*Width* (*measured from leaf tips*).—42.0 cm to 47.0 cm.

Leaves:

*Immature leaves*.—Length: 15.0 cm to 18.0 cm. Width: 10.0 cm to 12.0 cm. Color: Upper surface: About RHS N199A with red margin (RHS 185A). Lower surface: RHS N199A. Texture (both upper and lower surfaces): Shiny.

*Mature leaves*.—Length (fully expanded): 19.0 cm to 21.0 cm. Width: 13.0 cm to 14.0 cm. Shape: Ovate cordate. Apex: Acute. Base: Cordate. Leaf blade angle with the petiole: Between 100 degrees and 120 degrees. Leaf margin: Entire. Color: Upper surface: RHS 147A. Lower surface: RHS 146A. Texture (upper surface): Shiny, leathery, and thick. Blistering (upper surface): Absent. Venation: Pinnate veining; the mid-vein and primary veins (the veins that radiate out from the junction of petiole and leaf) protrude at the underside of the leaf blade. Venation color: Upper surface: RHS 144A. Lower surface: RHS 144B.

*Lobes*.—Present. Arrangement: Leaf blade has two lobes extending past the petiole. The lobes are non-touching. Length of lobes of mature leaf blades: 3.5 cm to 4.5 cm. Width of lobes of mature leaf blades: 5.5 cm to 6.5 cm. Distance from petiole/leaf junction to highest point on lobes of mature leaf: 3.0 cm to 4.0 cm.

*Petiole*.—Cross-section: Round. Diameter: 0.3 cm to 0.4 cm. Length: 24.0 cm to 26.0 cm for a mature leaf size. Color: Mature leaf: RHS 144A. Immature leaf: RHS 152A and 174A. Cataphyll color surrounding the petiole: Outside: Red: RHS 180B at base and RHS 180A toward the tip. Inside: Between RHS 180C and 180D.

*Geniculum*.—Length: 2.0 cm to 2.5 cm. Width: 0.4 cm to 0.5 cm. Color: RHS 144B.

Inflorescence:

*Arrangement*.—Single.

*Flowering habit* (*length of flowering season*).—Continuous.

*Number of inflorescences per plant*.—5 to 9.

*Fragrance*.—Absent.

*Longevity of inflorescence on plant*.—Over a year.

Spathe:

*Buds*.—The spathe is tightly rolled around the spadix and extrudes from the peduncle sheath.

*Arrangement*.—Spathe angle with the peduncle is between 105 degrees and 120 degrees; the spathe stands on a wiry peduncle about 5.0 cm to 10.0 cm above the foliage.

*Shape*.—Orbicular cordate.

*Apex*.—Mucronate.

*Base*.—Cordate.

*Texture*.—Shiny and blistered.

*Blistering*.—Weak.

*Margin*.—Undulated.

*Size*.—Length: 11.0 cm to 12.0 cm. Width: 11.0 cm to 12.0 cm.

*Lobes*.—Present. Arrangement: The spathe has two lobes extending past the peduncle. The lobes are non-touching. Length: 3.0 cm to 3.5 cm. Width: 5.0 cm to 6.0 cm.

*Color*.—Just fully open: Upper surface: RHS 45B. Lower surface: RHS 45C. This bright red color remains for a very long period, at least more than 30 weeks after opening.

Peduncle:

*Shape*.—Erect.

*Cross-section*.—Round.

*Length*.—32.0 cm to 35.0 cm.

*Diameter*.—0.4 cm to 0.5 cm.

*Color*.—RHS 152C with a touch of RHS 175D.

Flowering time:

*General*.—One small, rooted, untreated tissue culture plant of 8.0 cm tall will flower, depending on the season, after 42 to 46 weeks and 5 to 7 blossoms appear. More blossoms appear after some additional weeks so that a full flowering and commercial plant will have 8 to 9 bright red spathes. Smaller blossoms may occur on immature plants.

Spadix:

*Size*.—Length: 5.0 cm to 6.0 cm (depending on flower size). Width (at apex): 0.5 cm to 0.6 cm. Width (at base): 0.6 cm to 0.7 cm.

*Shape*.—Columnar.

*Angle from spadix tip to peduncle*.—160 degrees to 170 degrees.

*Texture*.—When the spathe is unfurling the spadix is smooth. When the spadix matures, small stigmata protrude. The stigmata are evenly distributed around the spadix. The spadix matures from base to top, slowly giving the spadix a somewhat rough appearance.

*Color*.—Immature: RHS 15A and RHS 153D at the tip. Mature: RHS NN155A. Ages to: RHS N144A.

Flowers:

*Quantity per spadix*.—170 to 220.

*Spadix flower arrangement*.—Bisexual, rounded in cross-section.

*Shape*.—Rounded.

*Size*.—Length: 0.05 cm to 0.10 cm. Diameter (maximum): 0.10 cm.

*Color*.—RHS 156D.

Reproductive organs:

*Stamens*.—Not visible.

*Pollen amount*.—Absent.

*Pistil*.—Quantity: 170 to 220. Length: Less than 0.01 cm. Color: RHS 156D.

*Style*.—Not observed to date.

*Stigma*.—Shape: Ovoid. Diameter: Less than 0.01 cm. Color: RHS 156D.

*Ovary*.—Rarely visible.

*Ovary color*.—Not measured.

Fruit and seed set: None observed to date.

Disease and pest resistance: No specific resistance or susceptibility observed to pathogens or pests common to *Anthurium* under commercial conditions.

COMPARISON WITH PARENTAL AND SIMILAR COMMERCIAL VARIETIES

'ANTHATEIP' differs from the female parent plant '16232-01' (unpatented) in that 'ANTHATEIP' has red cataphylls, ovate-cordate leaves, and orbicular-cordate spathes with mucronate apexes, whereas '16232-01' has green cataphylls with red tips, elliptical-cordate leaves, and cordate spathes with acuminate apexes.

'ANTHATEIP' differs from the male parent plant '10953-02' (unpatented) in that 'ANTHATEIP' has red cataphylls and orbicular-cordate spathes, whereas '10953-02' has green cataphylls with red tips and oblong-cordate spathes. Additionally, 'ANTHATEIP' has a larger angle of the spadix tip with the peduncle than '10953-02'.

'ANTHATEIP' differs from similar commercial variety 'ANTHBNEQ' (U.S. Plant Pat. No. 15,286) in that 'ANTHATEIP' has red cataphylls, acute leaf apexes, and immature leaves that are about RHS N199A with red margins of RHS 185A, whereas 'ANTHBNEQ' has cataphylls that are brown-red at the base and brown toward the tip, acuminate leaf apexes, and immature leaves that are RHS 147A.

'ANTHATEIP' differs from similar commercial variety 'ANTHOLYL' (U.S. Plant Pat. No. 20,283) in that 'ANTHATEIP' has red cataphylls, orbicular-cordate spathes, acute leaf apexes, and immature leaves that are about RHS N199A with red margins of RHS 185A, whereas 'ANTHOLYL' has green cataphylls with small reddish tips, oblong-cordate spathes, acuminate leaf apexes, and immature leaves that are RHS 137A.

I claim:

1. A new and distinct variety of *Anthurium* plant named 'ANTHATEIP', substantially as illustrated and described herein.

* * * * *